(12) United States Patent
Honda et al.

(10) Patent No.: US 10,007,976 B2
(45) Date of Patent: Jun. 26, 2018

(54) IMAGE PROCESSING APPARATUS, MEDICAL IMAGE DIAGNOSTIC APPARATUS, AND X-RAY DIAGNOSTIC APPARATUS

(71) Applicants: National Institute of Technology, Hachioji-shi (JP); Toshiba Medical Systems Corporation, Otawara-shi (JP)

(72) Inventors: Michitaka Honda, Takamatsu (JP); Kunio Shiraishi, Otawara (JP); Takuya Sakaguchi, Utsunomiya (JP)

(73) Assignees: National Institute of Technology, Hachioji-shi (JP); Toshiba Medical Systems Corporation, Otawara-shi (JP)

( * ) Notice: Subject to any disclaimer, the term of this patent is extended or adjusted under 35 U.S.C. 154(b) by 59 days.

(21) Appl. No.: 14/959,449

(22) Filed: Dec. 4, 2015

(65) Prior Publication Data
US 2016/0086319 A1   Mar. 24, 2016

Related U.S. Application Data

(63) Continuation of application No. PCT/JP2014/064999, filed on Jun. 5, 2014.

(30) Foreign Application Priority Data

Jun. 5, 2013  (JP) ................................ 2013-119276

(51) Int. Cl.
*G06T 5/50* (2006.01)
*A61B 6/00* (2006.01)
(Continued)

(52) U.S. Cl.
CPC ............... *G06T 5/50* (2013.01); *A61B 5/055* (2013.01); *A61B 6/00* (2013.01); *A61B 6/5211* (2013.01);
(Continued)

(58) Field of Classification Search
CPC ........... A61B 5/055; A61B 6/00; A61B 6/032; A61B 6/037; A61B 6/12; A61B 6/461;
(Continued)

(56) References Cited

U.S. PATENT DOCUMENTS

| 6,763,129 | B1 | 7/2004 | Honda et al. |
| 2003/0206231 | A1* | 11/2003 | Chen ................. H04N 1/00137 348/207.99 |

(Continued)

FOREIGN PATENT DOCUMENTS

| JP | 03-182233 | 8/1991 |
| JP | 2001-111835 | 4/2001 |

(Continued)

OTHER PUBLICATIONS

International Search Report dated Sep. 2, 2014 in PCT/JP2014/064999 filed Jun. 5, 2014 (with English translation).

(Continued)

*Primary Examiner* — Kenny Cese
(74) *Attorney, Agent, or Firm* — Oblon, McClelland, Maier & Neustadt, L.L.P.

(57) ABSTRACT

An image processing apparatus according to an embodiment includes a first frequency image generating circuitry, a second frequency image generating circuitry, a signal detecting circuitry, and a display image generating circuitry. The first frequency image generating circuitry performs, on an object pixel of processing, processing based on a pixel value of a neighboring pixel positioned close to the pixel to generate first frequency image data including a specific contrast component and a first frequency component on image data. The second frequency image generating circuitry performs processing of subtracting the first frequency image data from the image data to generate second frequency image data including a second frequency compo- (Continued)

nent. The signal detecting circuitry detects a linear signal derived from a linear structural object from the second frequency image data. The display image generating circuitry generates a display image according to the linear signal detected.

8 Claims, 13 Drawing Sheets

(51) Int. Cl.
| | |
|---|---|
| *G06T 5/00* | (2006.01) |
| *G06T 7/13* | (2017.01) |
| *A61B 5/055* | (2006.01) |
| *A61B 6/12* | (2006.01) |
| *A61B 8/00* | (2006.01) |
| *A61B 6/03* | (2006.01) |
| *A61B 8/08* | (2006.01) |

(52) U.S. Cl.
CPC .............. *G06T 5/002* (2013.01); *G06T 5/007* (2013.01); *G06T 5/009* (2013.01); *G06T 7/13* (2017.01); *A61B 6/032* (2013.01); *A61B 6/037* (2013.01); *A61B 6/12* (2013.01); *A61B 6/461* (2013.01); *A61B 8/00* (2013.01); *A61B 8/5215* (2013.01); *G06T 2207/10116* (2013.01); *G06T 2207/20192* (2013.01); *G06T 2207/20208* (2013.01); *G06T 2207/20224* (2013.01)

(58) Field of Classification Search
CPC ....... A61B 6/5211; A61B 8/00; A61B 8/5215; G06T 2207/10116; G06T 2207/20192; G06T 2207/20208; G06T 2207/20224; G06T 5/002; G06T 5/007; G06T 5/009; G06T 5/50; G06T 7/13

See application file for complete search history.

(56) References Cited

U.S. PATENT DOCUMENTS

| | | | |
|---|---|---|---|
| 2005/0123214 A1* | 6/2005 | Takahira | ................. G06T 5/004 382/266 |
| 2009/0161019 A1* | 6/2009 | Jang | ....................... H04N 9/646 348/663 |
| 2010/0020230 A1* | 1/2010 | Suzuki | ................. G06F 3/1415 348/441 |
| 2010/0104167 A1* | 4/2010 | Sakaguchi | ............... A61B 6/12 382/132 |
| 2011/0268368 A1 | 11/2011 | Toyoda et al. | |

FOREIGN PATENT DOCUMENTS

| | | |
|---|---|---|
| JP | 2006-230512 | 9/2006 |
| JP | 2012-61307 A | 3/2012 |
| JP | 2012-134576 A | 7/2012 |
| WO | WO 2010/086973 A1 | 8/2010 |

OTHER PUBLICATIONS

Masaki Otani, et al., "A Direction Detection Method of Line Pattern on the Noisy Background", IEICE Technical Report, vol. 109, (123), 2009, 8 pgs. (with English Abstract and partial English translation).

Office Action dated Jun. 20, 2017 in Japanese Patent Application No. 2013-119276.

* cited by examiner

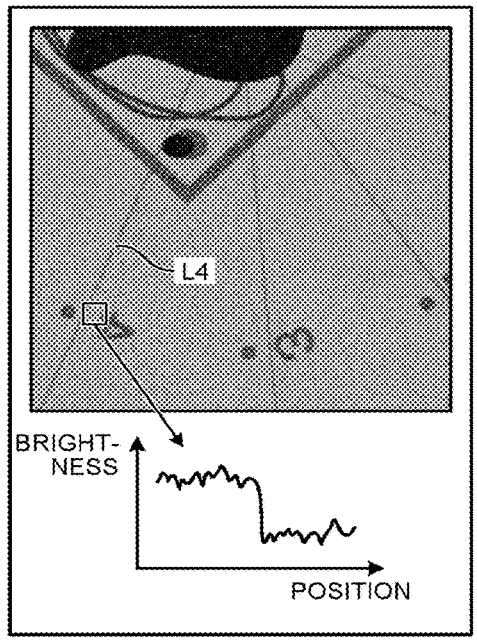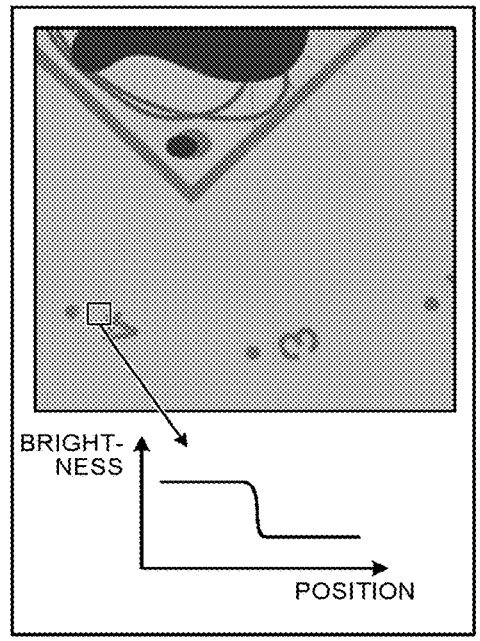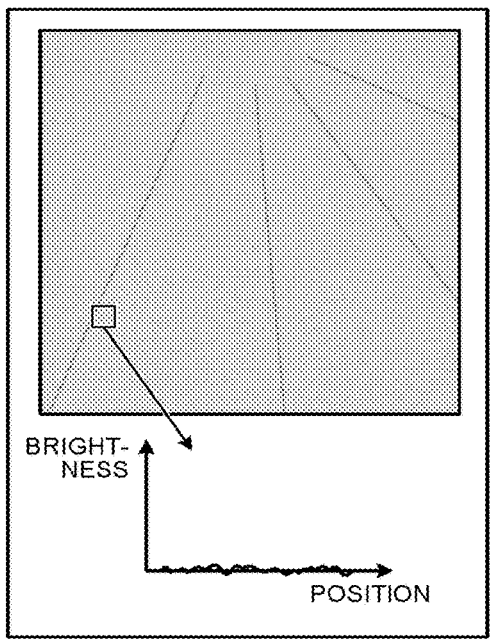

IMAGE PROCESSING APPARATUS, MEDICAL IMAGE DIAGNOSTIC APPARATUS, AND X-RAY DIAGNOSTIC APPARATUS

CROSS-REFERENCE TO RELATED APPLICATION

This application is a continuation of PCT international application Ser. No. PCT/JP2014/064999 filed on Jun. 5, 2014 which designates the United States, incorporated herein by reference, and which claims the benefit of priority from Japanese Patent Applications No. 2013-119276, filed on Jun. 5, 2013, incorporated herein by reference.

FIELD

Embodiments described herein relate generally to an image processing apparatus, a medical image diagnostic apparatus, and an X-ray diagnostic apparatus.

BACKGROUND

Various kinds of image processing are employed for facilitating observation of an object to be observed included in an image. For example, such image processing performed on an image including a linear signal serving as an observed object is known that emphasizes the linear signal and controls elements (such as a background) other than the linear signal by separating the linear signal from the elements other than the linear signal. As an example, such an image processing method is known that removes a low-frequency component from an image, extracts a high-frequency image including a high-frequency component where a linear signal is classified, detects the linear signal using the extracted high-frequency image, and performs emphasizing processing and the like on the detected linear signal.

Use of the above-described image processing method can, for example, accurately detect a linear structural object such as a catheter on a fluoroscopic image imaged by an X-ray diagnostic apparatus and display the object. With the above-described conventional technique, however, visibility of an image including a linear signal is likely to decrease.

BRIEF DESCRIPTION OF THE DRAWINGS

FIG. 4A to 4E are drawings that schematically illustrates processing performed by a first frequency image generating circuitry according to the first embodiment;

FIGS. 6A to 6C are drawings that schematically illustrate processing performed by a second frequency image generating circuitry according to the first embodiment;

DETAILED DESCRIPTION

According to an embodiment, an image processing apparatus includes processing circuitry. The processing circuitry is configured to perform, on an object pixel of processing, processing based on a pixel value of a neighboring pixel positioned close to the pixel to generate first frequency image data including a specific contrast component and a first frequency component on image data. The processing circuitry is configured to perform processing of subtracting the first frequency image data from the image data to generate second frequency image data including a second frequency component. The processing circuitry is configured to detect a linear signal derived from a linear structural object from the second frequency image data. The processing circuitry is configured to generate a display image according to the linear signal detected.

First Embodiment

Figure 1:
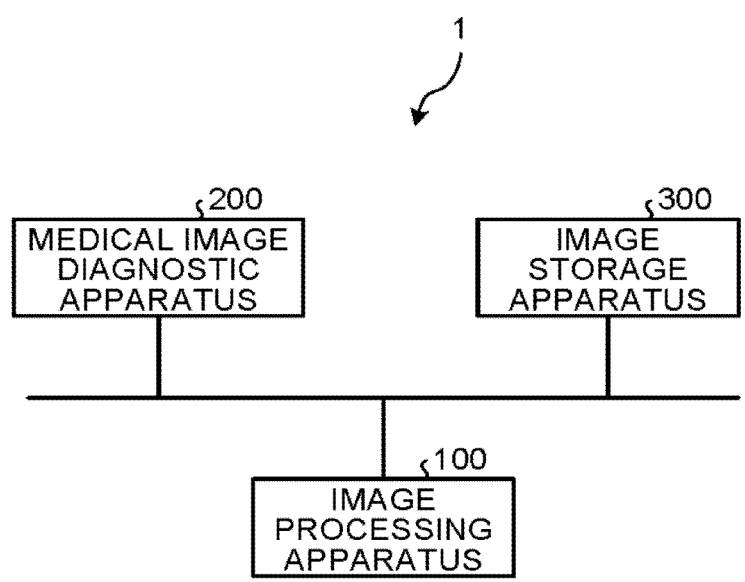
FIG. 1 is a drawing that illustrates an exemplary configuration of an image processing system according to a first embodiment.

Details of an image processing apparatus according to an embodiment will now be described. In a first embodiment, an image processing system including the image processing apparatus according to the embodiment will be described as an example. FIG. 1 is a drawing that illustrates an exemplary configuration of an image processing system 1 according to the first embodiment.

As FIG. 1 illustrates, the image processing system 1 according to the first embodiment includes an image processing apparatus 100, a medical image diagnostic apparatus 200, and an image storage apparatus 300. Apparatus illustrated in FIG. 1 are in a state of directly or indirectly communicating with one another via, for example, an inhospital local area network (LAN) deployed in a hospital. For example, if the image processing system 1 uses a picture archiving and communication system (PACS), the apparatus each transmit and receive medical images and others to and from one another in accordance with the digital imaging and communications in medicine (DICOM) standard.

Examples of the medical image diagnostic apparatus 200 include an X-ray diagnostic apparatus, an X-ray computed tomography (CT) apparatus, a magnetic resonance imaging (MRI) apparatus, an ultrasonic diagnostic apparatus, a single photon emission computed tomography (SPECT) apparatus, a positron emission computed tomography (PET) apparatus, a SPECT-CT apparatus where a SPECT apparatus and an X-ray CT apparatus are integrated, a PET-CT apparatus where a PET apparatus and an X-ray CT apparatus are integrated, and a group including these apparatus. The medical image diagnostic apparatus 200 collects medical images in response to the operation of a technician.

The medical image diagnostic apparatus 200 transmits collected image data to the image processing apparatus 100 and the image storage apparatus 300. In transmitting image data to the image storage apparatus 300, the medical image diagnostic apparatus 200 adds information such as a patient ID for identifying a patient, an examination ID for identifying an examination, an apparatus ID for identifying the medical image diagnostic apparatus 200, a series ID for identifying a photographing operation by the medical image diagnostic apparatus 200.

The image storage apparatus 300 is a database for storing medical images. Specifically, the image storage apparatus 300 stores image data, additional information of the image data, and others transmitted from the medical image diagnostic apparatus in a storage circuitry and keeps the data and information.

The image processing apparatus 100 acquires image data from the medical image diagnostic apparatus 200 or the image storage apparatus 300 and performs image processing for improving visibility of the image including a linear signal. A conventional technique where visibility of an image including a linear signal is decreased will now be described. As described above, in order to facilitate observation of a linear signal, the conventional technique detects a linear signal included in image data and performs emphasizing processing on the detected linear signal and control processing on signals other than the linear signal. In detecting a linear signal with this kind of image processing, such image processing is performed as preprocessing that removes a low-frequency component from image data so as to separate a high-frequency component including the linear signal and detects the linear signal from the separated high-frequency component.

If a high contrast component is included in the high-frequency image generated by removing the low-frequency component from the image data, the high contrast component may affect detection of the linear signal. FIGS. 2A to 2D are illustrative drawings of examples of detection of a linear signal according to the conventional technique. In FIGS. 2A to 2D, such a case is described as an example that detects a linear signal included in an X-ray image imaged by an X-ray diagnostic apparatus serving as a medical image diagnostic apparatus. A signal in a linear shape and expressed only in the black side (for example, an X-ray image(may be hereinafter referred to as a linear shadow).

Figure 2A:
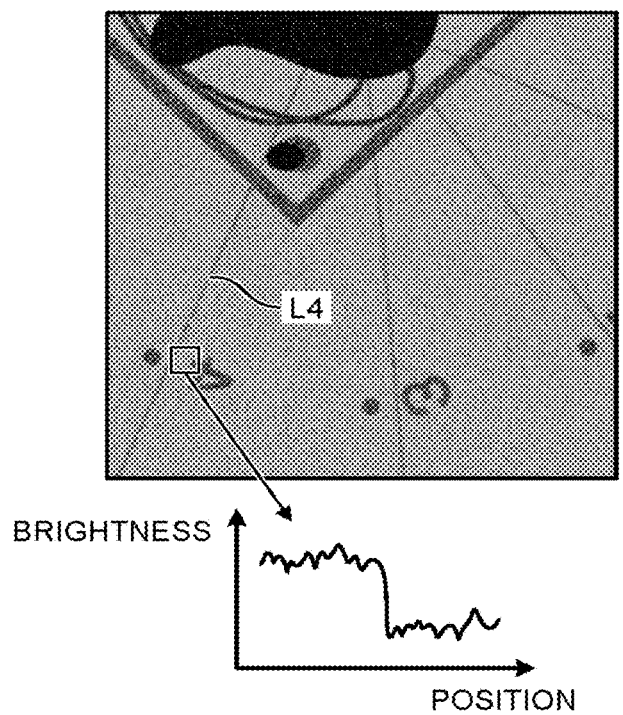
FIG. 2A is an illustrative drawing of an example of detection of a linear signal according to a conventional technique.
Figure 2B:
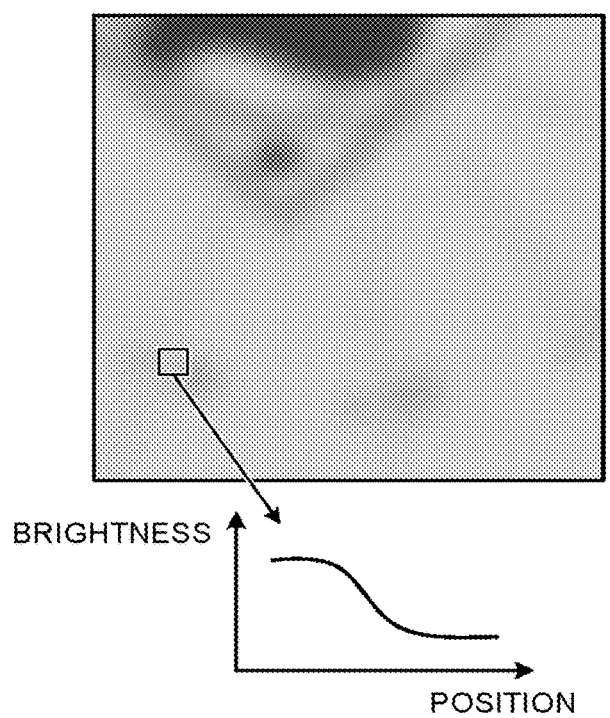
FIG. 2B is another illustrative drawing of an example of detection of the linear signal according to the conventional technique.
Figure 2C:
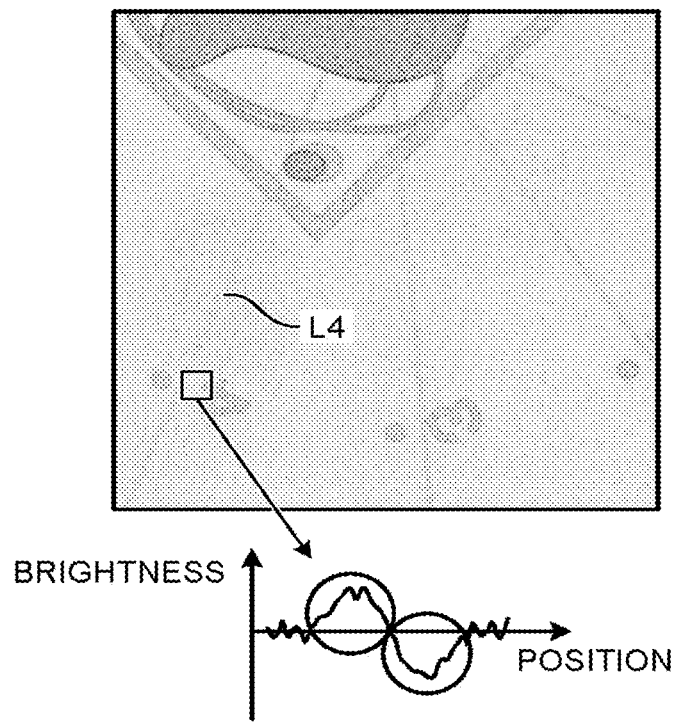
FIG. 2C is still another illustrative drawing of an example of detection of the linear signal according to the conventional technique.
Figure 2D:
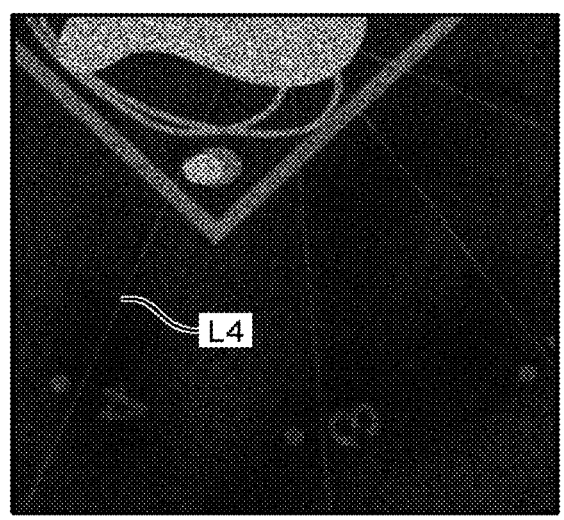
FIG. 2D is still another illustrative drawing of an example of detection of the linear signal according to the conventional technique.

In FIGS. 2A to 2D, FIG. 2A illustrates an X-ray image, FIG. 2B illustrates a low-frequency image of the X-ray image of FIG. 2A, FIG. 2C illustrates a high-frequency image of the X-ray image of FIG. 2A, and FIG. 2D illustrates a result of detection of a linear signal based on the high-frequency image of FIG. 2C. For example, for detecting a linear signal L4 indicated in the X-ray image of FIG. 2A, the conventional technique performs smoothing processing on the X-ray image and generates the low-frequency image of FIG. 2B.

The conventional technique subtracts the low-frequency image of FIG. 2B from the X-ray image of FIG. 2A and generates the high-frequency image of FIG. 2C. The conventional technique further performs detecting processing on the linear signal L4 in the generated high-frequency image and detects the linear signal L4 indicated in FIG. 2D. In this process of the conventional technique, a high contrast area such as numbers and dots in FIG. 2A affects a nearby linear signal.

An exemplary case of detecting the linear signal L4 is now described. For example, on the X-ray image of FIG. 2A, a high contrast area where a pixel level (brightness) sharply changes between pixels exists near the linear signal L4 as illustrated in the lower graph of FIG. 2A. The lower graph of FIG. 2A depicts a profile of pixel levels in the rectangular area on the X-ray image of FIG. 2A. In other words, the lower graph of FIG. 2A indicate brightness of a pixel (pixels from a white portion to a black portion) at each position in the rectangle.

By performing smoothing processing on the high contrast area, such a low-frequency image obtained where the high contrast area is indicated by a gently sloping profile as the lower graph of FIG. 2B. By performing subtraction processing on the X-ray image using such a low-frequency image, a high-frequency image including a high contrast component near the linear signal L4 is generated as illustrated in the lower graph of FIG. 2C. As illustrated in FIG. 2D, the linear signal L4 is therefore less likely to be detected near the high contrast area, which consequently decreases visibility of the image including the linear signal.

In displaying an X-ray image with a guidewire emphasized, for example, the guidewire arranged near an area where a bolt, a staple, and the like are buried may be undetectable or overemphasised.

The image processing apparatus 100 according to the first embodiment thus generate a low-frequency image including a high contrast component, subtracts the generated low-frequency image from image data, and generates a high-frequency image including no high contrast components. Visibility of the image including a linear signal is thus improved.

Figure 3:
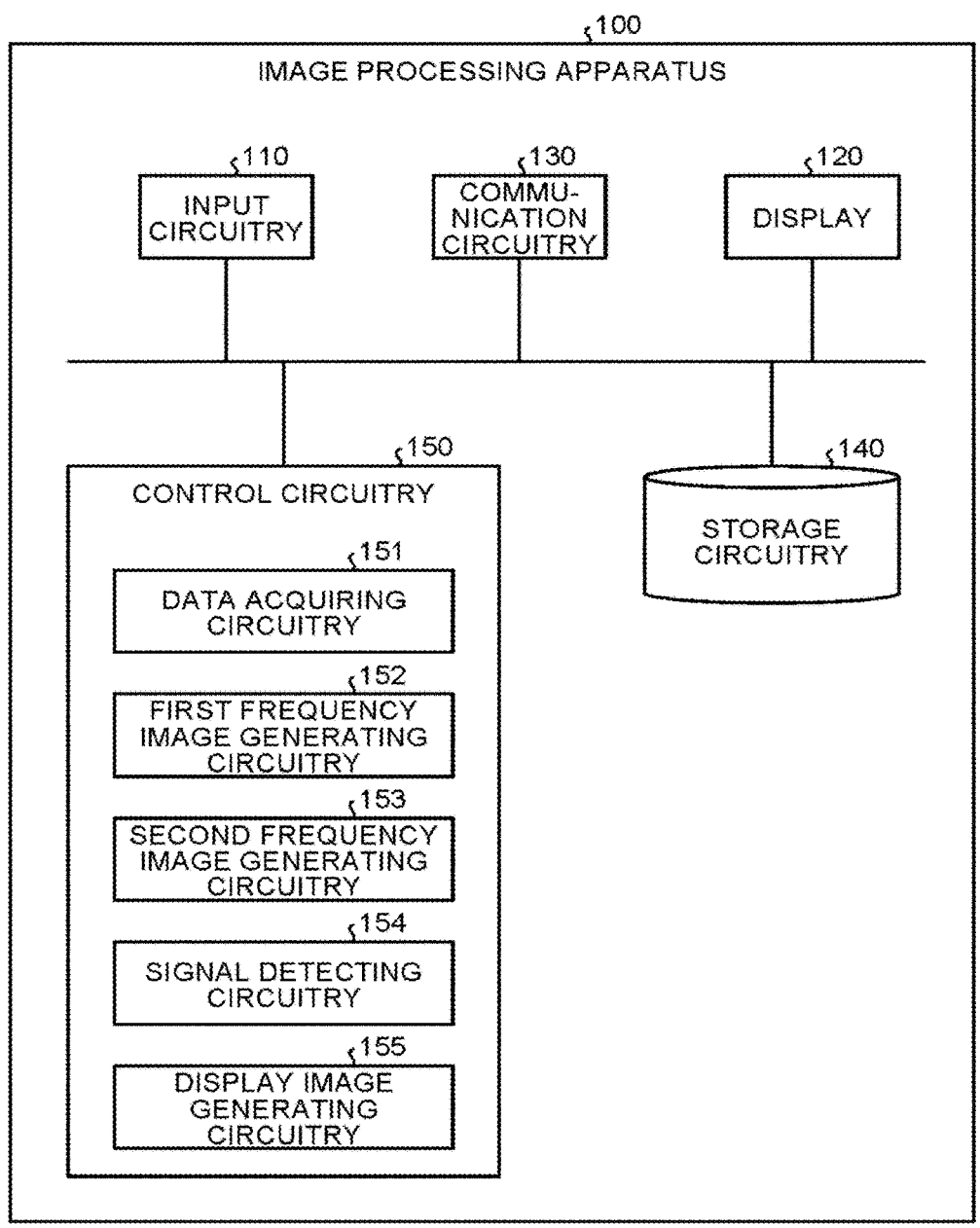
FIG. 3 is a drawing that illustrates an exemplary configuration of an image processing apparatus according to the first. embodiment.

FIG. 3 is a drawing that illustrates an exemplary configuration of the image processing apparatus 100 according to the first embodiment. As FIG. 3 illustrates, the image processing apparatus 100 includes an input circuitry 110, a display 120, a communication circuitry 130, a storage circuitry 140, and a control circuitry 150. Examples of the image processing apparatus 100 include a workstation and any personal computer, and the image processing apparatus 100 is connected with the medical image diagnostic apparatus 200, the image storage apparatus 300, and others via a network.

Examples of the input circuitry 110 include a mouse, a keyboard, and a trackball, and The input circuitry 110 receives various kinds of operation inputs to the image processing apparatus 100 from an operator. Specifically, the input circuitry 110 receives an input for acquiring image data and the like.

Examples of the display 120 include a liquid crystal panel serving as a monitor, and the display 120 displays various kinds of information. Specifically, the display 120 displays results of processing performed by a graphical user interface (GUI) for receiving various kinds of operations from an operator and the later-described control circuitry 150. Examples of the communication circuitry 130 include a network interface card (NIC), and the communication circuitry 130 communicates with other apparatus.

Examples of the storage circuitry 140 include a semiconductor memory element such as a random access memory (RAM) and a flash memory and a storage device such as a hard disk and an optical disk. The storage circuitry 140 stores, for example, image data of a medical image acquired by the later-described control circuitry 150. The storage circuitry 140 further stores various kinds of information used by the later-described control circuitry 150. For example, the storage circuitry 140 stores threshold information and others used by the later-described control circuitry 150 when generating a low-frequency image. The threshold information will be described later in detail.

Examples of the control circuitry 150 include an electronic circuit such as a central processing unit (CPU), a micro processing unit (MPU) and an integrated circuit such as an application specific integrated circuit (ASIC) and a field programmable gate array (FPGA). The control circuitry 150 performs overall control on the image processing apparatus 100. The control circuitry 150 includes, for example, a data acquiring circuitry 151, a first frequency image generating circuitry 152, a second frequency image generating circuitry 153, a signal detecting circuitry 154, and a display image generating circuitry 155 as illustrated in FIG. 3.

The data acquiring circuitry 151 acquires data from the medical image diagnostic apparatus 200 or the image storage apparatus 300 via the communication circuitry 130. Specifically, the data acquiring circuitry 151 acquires image data and the like from the medical image diagnostic apparatus 200 or the image storage apparatus 300 according to an instruction given by an operator through the input circuitry 110 and stores the data in the storage circuitry 140. The data acquiring circuitry 151 stores, for example, image data and the like of a medical image including a linear signal.

Figure 4A:
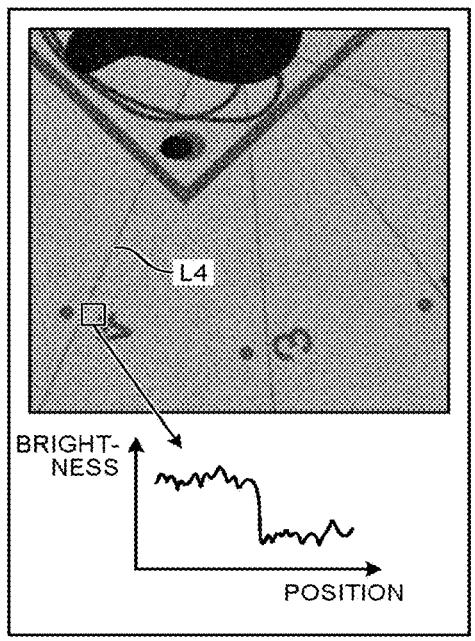
Figure 4B:
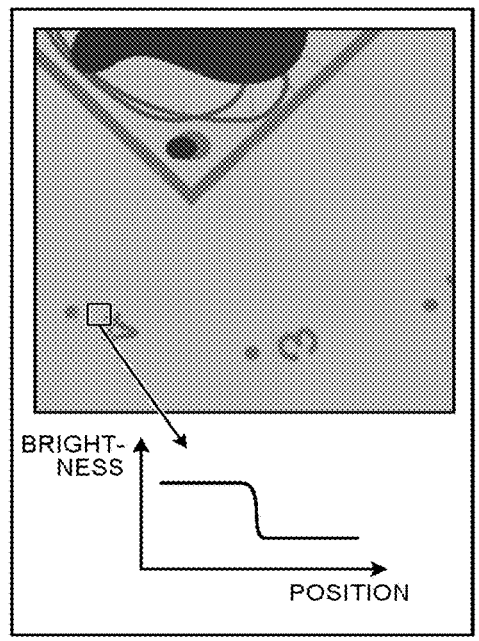

The first frequency image generating circuitry 152 generates first frequency image data including a specific contrast component and a first frequency component on image data. Specifically, the first frequency image generating circuitry 152 generates the first frequency image data including the first frequency component, which is a frequency component lower than a second frequency component, and the specific contrast. The first frequency image generating circuitry 152 performs, on an object pixel of processing, processing based on the pixel value of a neighboring pixel positioned close to the pixel and generates the first frequency image data. Specifically, the first frequency image generating circuitry 152 includes, in the first frequency image data, as the specific contrast component, a contrast component of when the difference in pixel values between pixels positioned close to each other on the image data exceeds a specific threshold. FIG. 4A to 4B are drawings that schematically illustrates processing performed by the first frequency image generating circuitry 152 according to the first embodiment. FIG. 4A illustrates an X-ray image including a linear signal whereas FIG. 4B illustrates a low-frequency image.

For example, the first frequency image generating circuitry 152 performs specific processing on the X-ray image illustrated in FIG. 4A and generates the low-frequency image including a high contrast component as illustrated in FIG. 4B. In other words, the first frequency image generating circuitry 152 generates a low-frequency image including a high contrast area where, similarly with the X-ray image of FIG. 4A, brightness sharply changes between pixels as indicated in the lower graph of FIG. 4B.

The first frequency image generating circuitry according to the first embodiment sets, as the pixel value of each pixel on image data, an average of pixel values of neighboring pixels, the pixel values of which fall within a range based on the standard deviation of noise, among neighboring pixels positioned close to the pixel and generates the first frequency image data. In other words, the first frequency image generating circuitry 152 generates a low-frequency image by smoothing each pixel on the image data using a pixel value with higher similarity to the pixel value of the pixel.

Figure 5A:
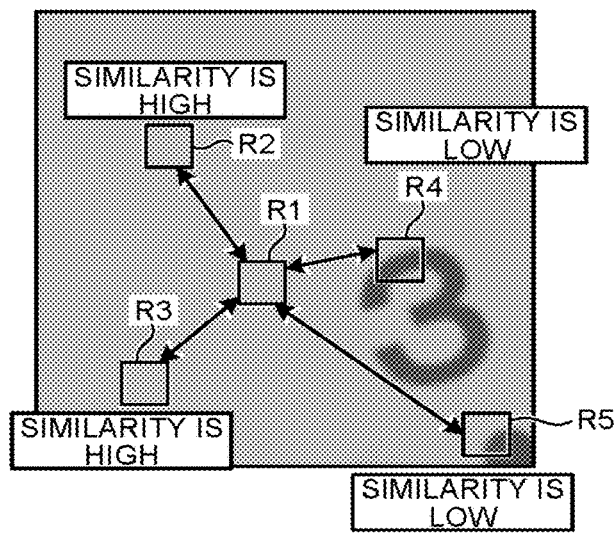
FIG. 5A is a drawing that illustrates exemplary processing performed by the first frequency image generating circuitry according to the first embodiment.
Figure 5B:
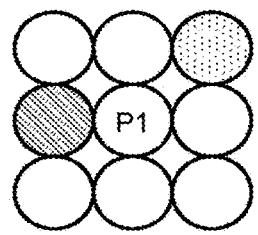
FIG. 5B is another drawing that illustrates exemplary processing performed by the first frequency image generating circuitry according to the first embodiment.
Figure 5C:
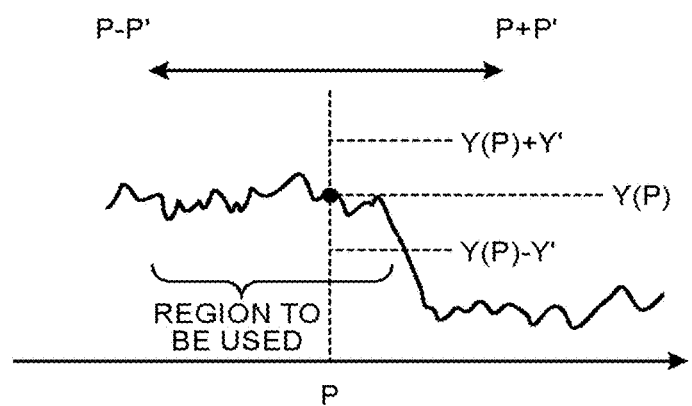
FIG. 5C is still another drawing that illustrates exemplary processing performed by the first frequency image generating circuitry according to the first embodiment.

FIGS. 5A to 5C are drawings that illustrate exemplary processing performed by the first frequency image generating circuitry 152 according to the first embodiment. For example, as illustrated in FIG. 5A, in the case of smoothing a region R1, the first frequency image generating circuitry 152 uses regions R2 and R3 having higher similarity to the region R1 in pixel values instead of using regions R4 and R5 having lower similarity to the region R1 in pixel values. As an example, as illustrated in FIG. 5B, in the case of smoothing an object pixel P1 to be smoothed, the first frequency image generating circuitry 152 uses a pixel value of a pixel with higher similarity from among pixels surrounding the object pixel P1, for example. Specifically, the first frequency image generating circuitry 152 smooths the object pixel P1 of FIG. 5B using pixels other than the pixel in the left middle position and the pixel in the right upper position.

The first frequency image generating circuitry 152 determines similarity based on a specific threshold. For example, the first frequency image generating circuitry 152 determines similarity of an object pixel based on statistical dispersion (the quantum mottle) of the pixel value. Specifically, as illustrated in FIG. 5C, the first frequency image generating circuitry 152 determines similarity based on a threshold "Y'" defined using the standard deviation of noise with respect to a pixel value "Y(P)" of an object pixel "P" and defines a region to be used. For example, the first frequency image generating circuitry 152 determines similarity using "3 to 6σ (that is, three to six times of the standard deviation "1σ")" as the threshold "Y'". In this case, if the pixel value of a pixel among pixels surrounding the object image "P" is between "Y(P)+Y'" and "Y(P)−Y'", the first frequency image generating circuitry 152 determines the similarity to be high. On the other hand, if the pixel value of a pixel among the pixels surrounding the object image "P" exceeds "Y(P)+Y'" or is less than "Y(P)−Y'", the first frequency image generating circuitry 152 determines the similarity to be low and does not use the pixel value of the pixel for smoothing processing.

With this process, for example, a white pixel on X-ray image is smoothed using only the pixel values of white pixels whereas a black pixel is smoothed using only black pixels. In this manner, as illustrated in FIG. 4B, the first frequency image generating circuitry 152 can generate a low-frequency image including a high contrast component where the brightness between pixels sharply changes. It should be noted that the above-described threshold "3 to 6σ" is only an example, and embodiments are not limited to this threshold. In other words, any threshold can be determined by a user or the like.

Threshold information such as the above-described threshold "3 to 6σ" is preliminarily stored in the storage circuitry 140. Information about the standard deviation of noise based on a pixel value is also preliminarily stored in the storage circuitry 140.

Referring back to FIG. 3, the second frequency image generating circuitry 153 performs processing of subtracting the first frequency image data from image data and generates second frequency image data including a second frequency component. Specifically, the second frequency image generating circuitry 153 subtracts the first frequency image data from image data and generates the second frequency image data including a frequency component higher than the first frequency component.

FIG. 6A to 6C are drawings that schematically illustrates processing performed by the second frequency image generating circuitry 153 according to the first embodiment. In FIG. 6A to 6C, a high-frequency image (FIG. 6C) is illustrated, the high-frequency image being generated by subtracting a low-frequency image (FIG. 6B) illustrated in FIG. 4B from an X-ray image (FIG. 6A) illustrated in FIG. 4A. More specifically, the second frequency image generating circuitry 153 subtracts the low-frequency image including a high contrast component from the X-ray image and generates the nigh-frequency image including no high contrast components as illustrated in FIG. 6C, for example.

Figure 7A:
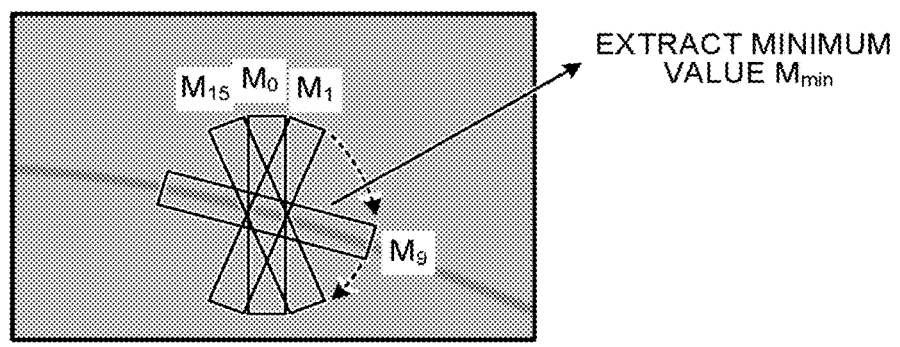
FIG. 7A is an illustrative drawing of an example of detection of a linear signal by a signal detecting circuitry according to the first embodiment.
Figure 7B:
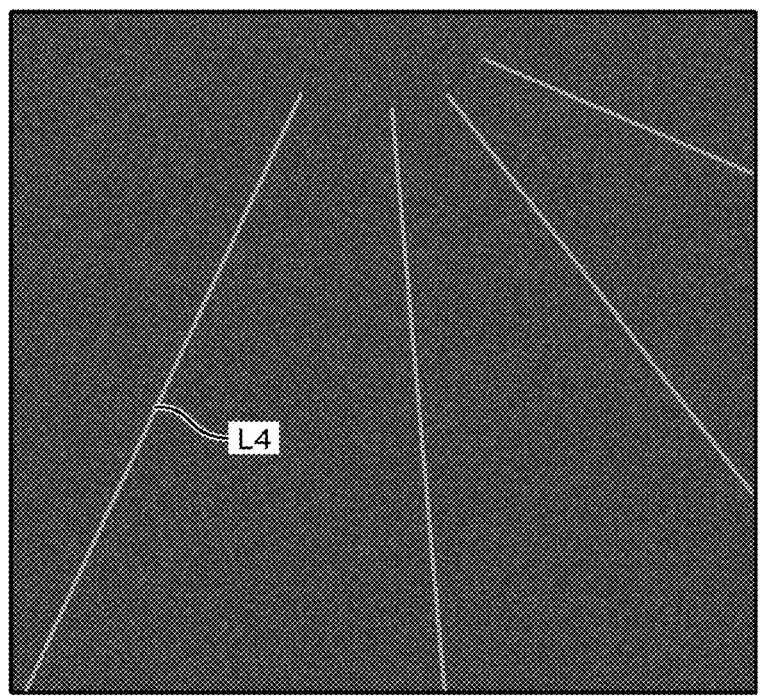
FIG. 7B is another illustrative drawing of an example of detection of a linear signal by the signal detecting circuitry according to the first embodiment.

Referring back to FIG. 3, the signal detecting circuitry 154 detects a linear signal derived from a linear structural object from the second frequency image data. Specifically, the signal detecting circuitry 154 detects a linear signal from the high-frequency image generated by the second frequency image generating circuitry 153. FIGS. 7 and 7B are illustrative drawings of examples of detection of the linear signal by the signal detecting circuitry 154 according to the first embodiment. FIG. 7A illustrates an exemplary method with which the signal detecting circuitry 154 detects a linear signal, and FIG. 7B is a drawing that illustrates a result of detecting processing performed by the signal detecting circuitry 154.

For example, as Illustrated in FIG. 7A, the signal detecting circuitry 154 detects a linear signal with template matching using a template in a specific shape (such as a rectangular shape). As an example, as illustrated in FIG. 7A, the signal detecting circuitry 154 rotates the template in 16 directions of $M_0$ to $M_{15}$ for each pixel and detects a linear signal based on the pixel values of pixel included in the template of each position. In other words, the signal detecting circuitry 154 calculates the average value of pixel values of pixels included in a template at each position of $M_0$ to $M_{15}$ and detects a linear signal based on the calculated average values.

For example, in the case of detecting a linear shadow as a detected object composed only of signals in the black side, the signal detecting circuitry 154 extracts, as illustrated in FIG. 7A, a template $M_9$ where the average of pixel values is a minimum value $M_{min}$. The signal detecting circuitry 154 thereafter calculates the average of vectors in the region of the extracted template $M_9$ and calculates the direction and the intensity of the linear shadow. The signal detecting circuitry 154 performs the above-described processing on all the pixels and, as illustrated in FIG. 7B, detects all linear signals including the linear signal L4. The 16 rotation directions are indicated as an example, and embodiments are not limited to the number of directions. In other words, a user can apply any number of rotation directions.

The case of detecting a linear shadow has been described above as an example; however, embodiments are not limited to this case. For example, the embodiments may be applied to the case of detecting a linear signal with a signal in the white side. In this case, a template where the average of pixel values is a maximum value $M_{max}$ is extracted in a determination using a template.

Referring back to FIG. 3, the display image generating circuitry 155 generates a display image based on the linear signal detected by the signal detecting circuitry 154. For example, the display image generating circuitry 155 generates a display image where the linear signal detected by the signal detecting circuitry 154 is emphasized or a display image where signals other than the linear signal are controlled.

As described above, the image processing apparatus 100 acquires image data of a medical image including a linear signal and generates a low-frequency image including a high contrast component. The image processing apparatus 100 performs processing of subtracting the generated low-frequency image from the image data and generates a high-frequency image including no high contrast components. The image processing apparatus 100 detects a linear signal from the generated high-frequency image and generates a display image. This manner consequently improves visibility of the image including the linear signal. The series of processing can be performed on a stored image and can also be performed on a real-time basis.

For example, the data acquiring circuitry 151 acquires image data of a medical image including a linear signal generated by the medical image diagnostic apparatus 200 in real time. The first frequency image generating circuitry 152, the second frequency image generating circuitry 153, the signal detecting circuitry 154, and the display image generating circuitry 155 each perform processing described above, thereby generating a display image. The display 120 thereafter displays the display image. If the image data of a medical image is serially generated video image data, every time a frame of the video image data is generated, the frame is acquired. Each of the above-described circuitry performs processing on each of the generated frames, and a display image is sequentially generated and displayed. With this process, the image processing apparatus 100 can generate and display a video image including a linear signal with higher visibility.

As an example, the image processing apparatus 100 performs the above-described processing on an X-ray image including a linear structural object such as a guidewire and a catheter inserted into a subject. Specifically, during a procedure using a guidewire, a catheter, or the like, the data acquiring circuitry 151 acquires an X-ray image (a frame) including a linear signal derived from the linear structural object such as the guidewire and the catheter from an X-ray diagnostic apparatus. The above-described circuitry each sequentially perform processing on each of the frames, which sequentially generates display images. The display 120 sequentially displays the sequentially generated display images. With this process, the image processing apparatus 100 can display an X-ray image with higher visibility of the guidewire, the catheter, or the like to a doctor and others performing a procedure using the guidewire, the catheter, or the like.

For example, the above-described processing may be performed on an X-ray image where a guidewire or a catheter is inserted near a bone. The display 120 thereafter displays a display image including the guidewire or the catheter inserted near the bone of the subject. This process can improve visibility of the X-ray image observation of which has been difficult.

Figure 8:
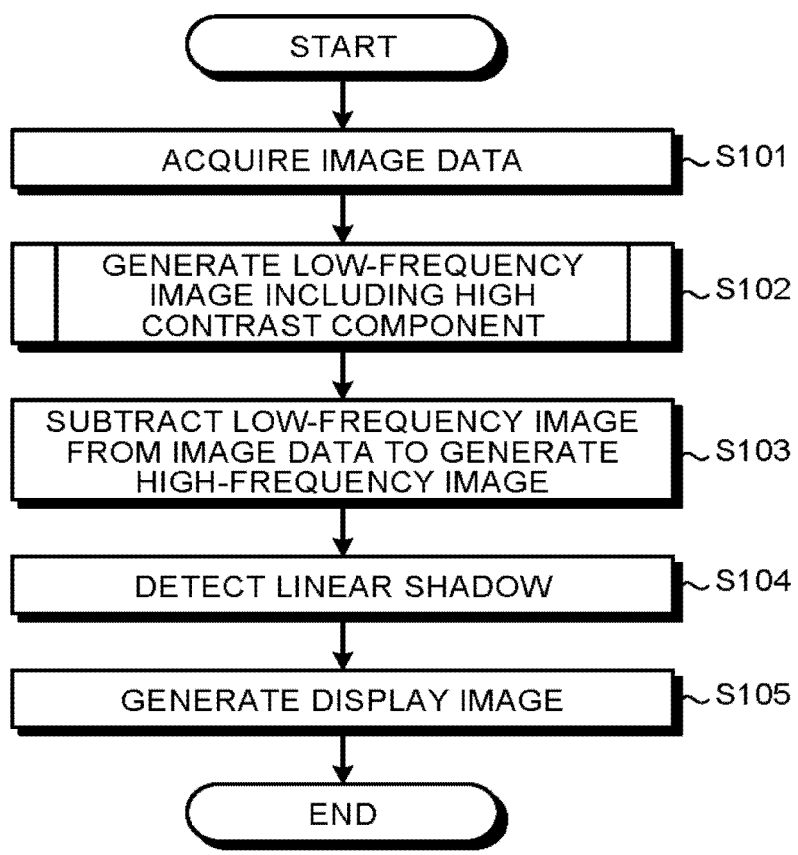
FIG. 8 is a flowchart that illustrates a procedure of linear signal detecting processing performed by the image processing apparatus according to the first embodiment.

Next, a procedure of the processing performed by the image processing apparatus 100 according to the first embodiment will now be described with reference to FIGS. 8 and 9. FIG. 8 is a flowchart that illustrates a procedure of a linear signal detecting processing performed by the image processing apparatus 100 according to the first embodiment. FIG. 8 illustrates such a case where a linear shadow is detected as a linear signal.

As FIG. 8 illustrates, with the image processing apparatus 100 according to the first embodiment, the acquiring circuitry 151 acquires image data (Step S101). The first frequency image generating circuitry 152 generates a low-frequency image including a high contrast component (Step S102). The second frequency image generating circuitry 153 thereafter subtracts the low-frequency image from the image data and generates a high-frequency image including no high contrast images (Step S103).

When the high-frequency image is generated, the signal detecting circuitry 154 detects a linear shadow (Step S104). The display image generating circuitry 155 generates a display image using the detected linear shadow (Step S105).

Figure 9:
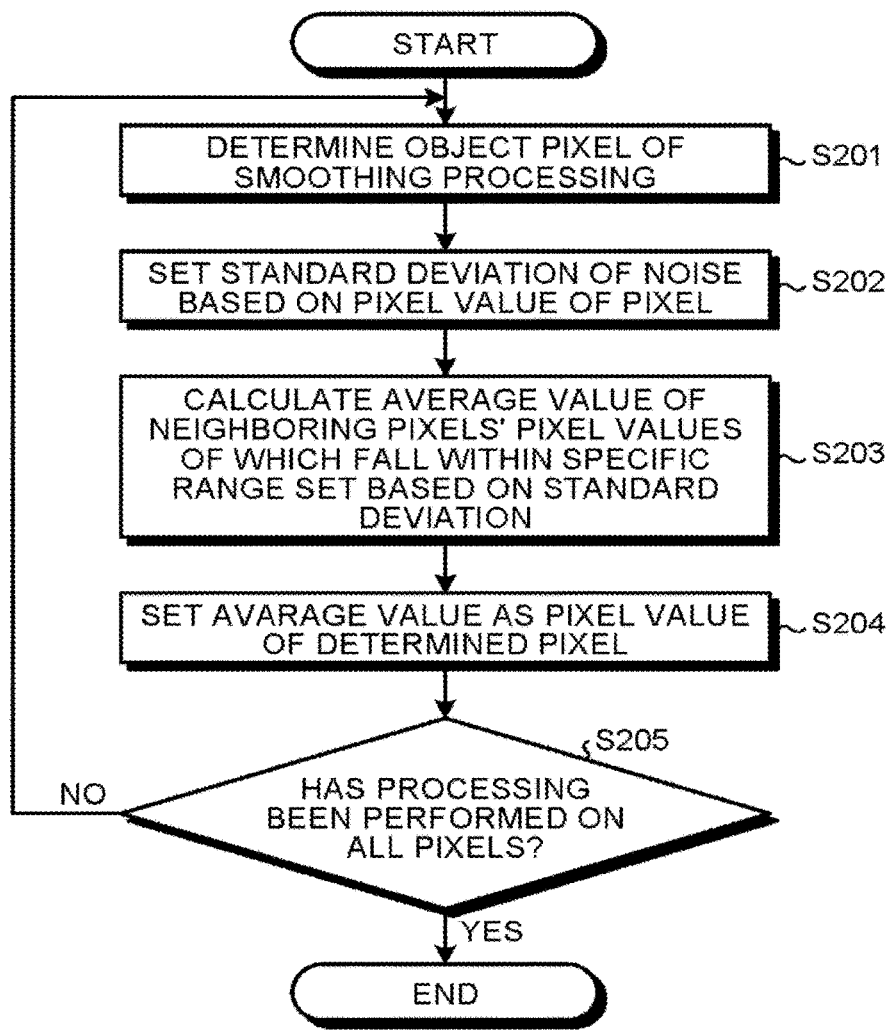
FIG. 9 is a flowchart that illustrates a procedure of low frequency image generating processing performed by the first frequency image generating circuitry according to the first embodiment.

FIG. 9 is a flowchart that illustrates a procedure of a low-frequency image generating processing performed by the first frequency image generating circuitry 152 according to the first embodiment. FIG. 9 illustrates processing equivalent to Step S102 in the flowchart of FIG. 8. As FIG. 9 illustrates, with the image processing apparatus 100 according to the first embodiment, when image data is acquired, the first frequency image generating circuitry 152 determines an object pixel of smoothing processing (Step S201).

The first frequency image generating circuitry 152 sets the standard deviation of noise based on the pixel value the object pixel of smoothing processing (Step S202). The first frequency image generating circuitry 152 calculates the average value of neighboring pixels, the pixel values of which fall within a specific range based on the standard deviation, among neighboring pixels positioned close to the object pixel (Step S203).

The first frequency image generating circuitry 152 sets the calculated average value as a pixel value of the determined pixel (Step S204) and determines whether the processing has been performed on all pixels (Step S205). If the first frequency image generating circuitry 152 determines that the processing has not yet been performed on all pixels (No at Step S205), the first frequency image generating circuitry 152 returns the process to Step S201 and selects another pixel to be an object. If the first frequency image generating circuitry 152 determines that the processing has been performed on all pixels (Yes at Step S205), the first frequency image generating circuitry 152 ends the processing.

As described above, according to the first embodiment, the first frequency image generating circuitry 152 generates first frequency image data including a specific contrast component and a first frequency component on image data. The second frequency image generating circuitry 153 performs processing of subtracting the first frequency image data from the image data and generates second frequency image data including a second frequency component. The signal detecting circuitry 154 detects a linear signal derived from a linear structural object from the second frequency image data. The display image generating circuitry 155 generates a display image according to the linear signal detected by the signal detecting circuitry 154. Consequently, the image processing apparatus 100 according to the first embodiment can detect the linear signal using the second frequency image including no contrasts, and visibility of the image including the linear signal can be accordingly improved.

Furthermore, according to the first embodiment, the first frequency image generating circuitry 152 determines a frequency component lower than the second frequency component to be the first frequency component and generates the first frequency image data including the first frequency component and a specific contrast. The second frequency image generating circuitry 153 subtracts the first frequency image data from the image data and generates the second frequency image data including a frequency component higher than the first frequency component. In this manner, the image processing apparatus 100 according the first embodiment can detect a linear signal.

According to the first embodiment, the first frequency image generating circuitry 152 includes, in the first frequency image data, a contrast component of when the difference in pixel values between pixels positioned close to each other on image data exceeds a specific threshold as the specific contrast component. The image processing apparatus 100 according to the first embodiment can thus generate the first frequency image including a high contrast component.

According to the first embodiment, the first frequency image generating circuitry 152 sets, as the pixel value of each pixel on image data, the average of pixel values of neighboring pixels, the pixel values of which fall within a range based on the standard deviation of noise, among neighboring pixels positioned close to the pixel and generates the first frequency image data. In this manner, the image processing apparatus 100 according to the first embodiment can easily generate a low-frequency image including a high contrast component.

Second Embodiment

In the above-described first embodiment, such a case has been described where a low-frequency image is generated by using the standard deviation of a pixel value. In a second embodiment, such a case will be described that generates a low-frequency image with edge preserving smoothing processing. The image processing apparatus 100 according to the second embodiment differs from the image processing apparatus 100 according to the first embodiment in the details of processing performed by the first frequency image generating circuitry 152. The details will be mainly described as follows.

Figure 10:
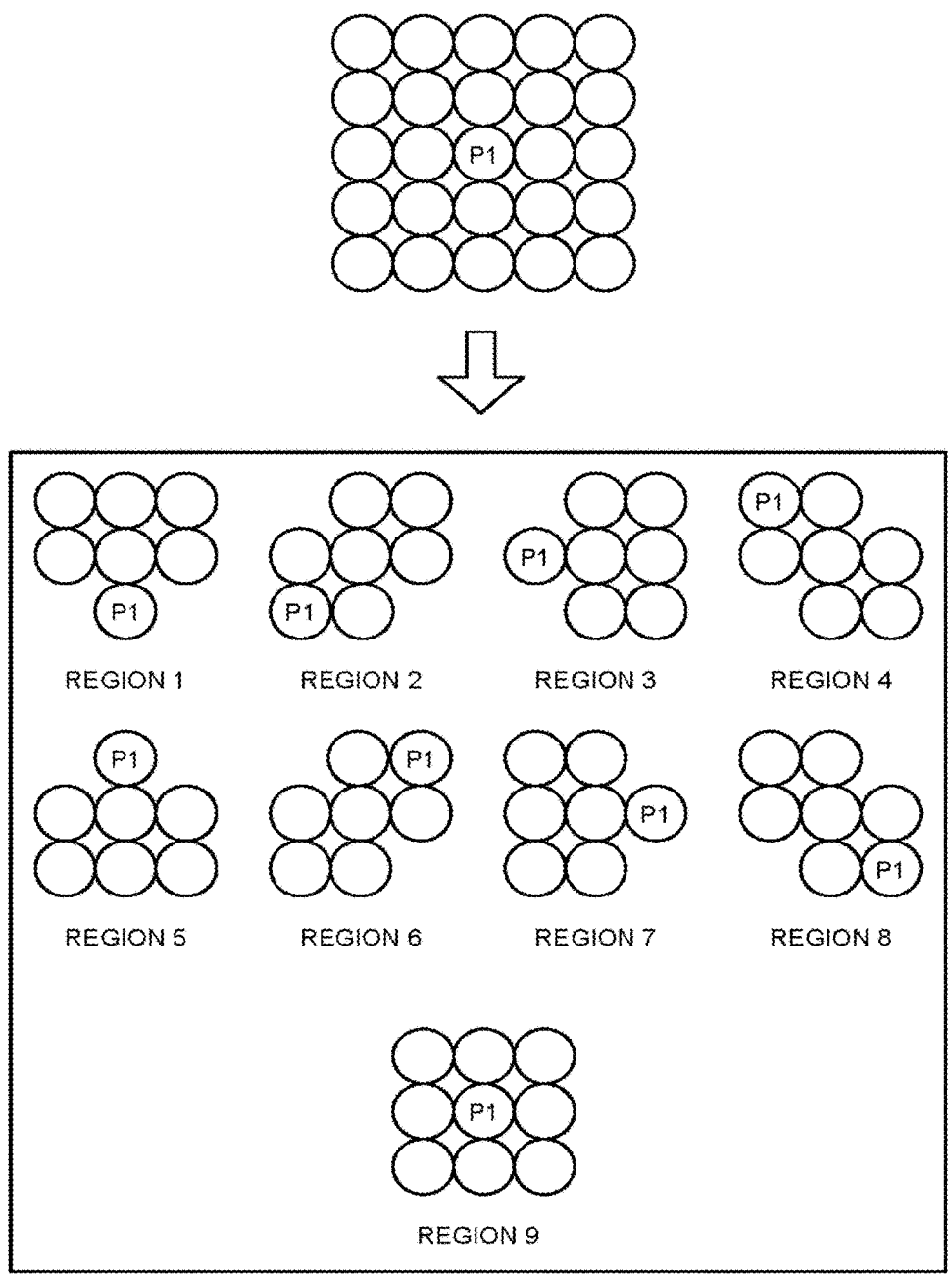
FIG. 10 is an illustrative drawing of an example of processing performed by the first frequency image generating circuitry according to a second embodiment.

The first frequency image generating circuitry 152 according to the second embodiment performs edge preserving smoothing processing on each pixel on image data and generates first frequency image data. FIG. 10 is an illustrative drawing of an example of processing performed by the first frequency image generating circuitry 152 according to the second embodiment.

For example, as illustrated in FIG. 10, the first frequency image generating circuitry 152 according to the second embodiment performs edge preserving smoothing processing on neighboring pixels of 5×5 with respect to a pixel P1 as an object of smoothing processing. As an example, as illustrated in FIG. 10, the first frequency image generating circuit 152 calculates the average and the variance of pixel values in each of nine regions, which are parts of the 5×5 neighboring pixels, each consisting of seven pixels including the object pixel P1. The first frequency image generating circuitry 152 extracts a region with the smallest variance from the regions 1 to 9 and sets the average value of the extracted region as a pixel value of the object pixel P1.

The first frequency image generating circuitry 152 sequentially performs the above-described processing on all pixels included in the image data with each of the pixels ac an object pixel. The first frequency image generating circuitry 152 generates the image, as a low-frequency image, in which pixel values have been set by performing the processing on all the pixels. With this process, such a low-frequency image is generated that includes a high contrast component.

The case illustrated in FIG. 10 is only an example, and embodiments are not limited to this case. In other words, neighboring pixels are not limited to pixels of 5×5 and may be composed of pixels of 3×3 or 7×7, for example. The region on which the average and the variance of pixel values are calculated is not limited to the regions illustrated in FIG. 10, and any change can be made.

Figure 11:
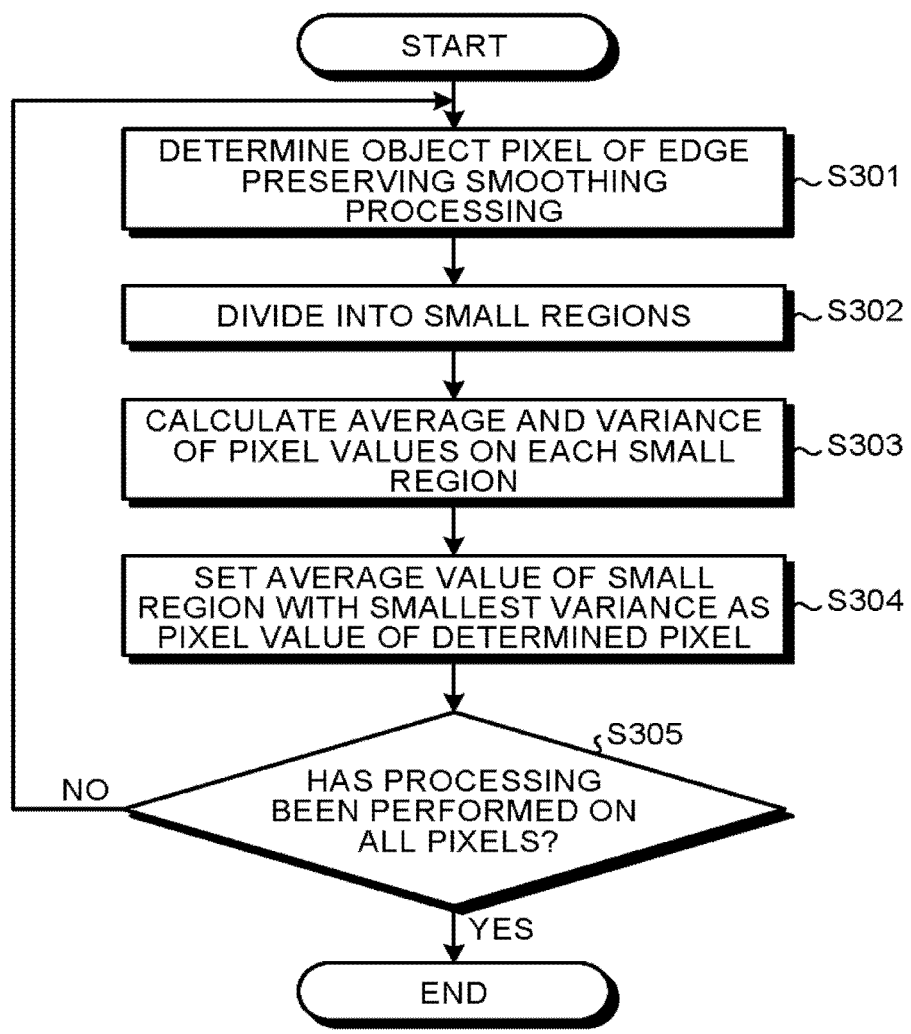
FIG. 11 is a flowchart that illustrates a procedure frequency image generating processing performed by the first frequency image generating circuitry according to the second embodiment.

Next, a procedure of processing performed by the image processing apparatus 100 according to the second embodiment will now be described with reference FIG. 11. FIG. 11 is a flowchart that illustrates a procedure of low-frequency image generating processing performed by the first frequency image generating circuitry 152 according to the second embodiment. FIG. 11 illustrates processing equivalent to Step S102 in the flowchart of FIG. 8. As illustrated in FIG. 11, with the image processing apparatus 100 according to the second embodiment, upon acquisition of image data, the first frequency image generating circuitry 152 determines an object pixel of edge preserving smoothing processing (Step S301).

The first frequency image generating circuitry 152 divides neighboring pixels including the determined pixel into specific small regions (Step S302). The first frequency image generating circuitry 152 thereafter calculates the average and the variance of pixel values on each of the divided small regions (Step S303).

The first frequency image generating circuitry 152 extracts a small region with the smallest variance from among the small regions and sets the average value in the extracted small region as a pixel value of the determined pixel (Step S304) and determines whether the processing has been performed on all the pixels (Step S305). If the first frequency image generating circuitry 152 determines that the processing has not yet been performed on all pixels (No at Step S305), the first frequency image generating circuitry 152 returns the process back to Step S301 and determines another pixel to be an object. If the first frequency image generating circuitry 152 determines that the processing has been performed on all pixels (Yes at Step S305), the first frequency image generating circuitry 152 ends the processing.

According to the above-described second embodiment, the first frequency image generating circuitry 152 performs edge preserving smoothing processing on each pixel on image data and generates the first frequency image data. In this manner, the image processing apparatus 100 according to the second embodiment can easily generate the first frequency image including a high contrast component.

Third Embodiment

While the first and the second embodiments have been described, the embodiments may be implemented in various embodiments different from the above-described first and second embodiments.

In each of the above-described first and second embodiments, such a case have been described where two frequency images, a low-frequency image and a high-frequency image, are used; however, embodiments are not limited to this case. For example, such a case may be conceived where three or more frequency images (such as the highest, the middle, and the lowest frequency images) are generated and subtraction processing is performed between these images. In this case, the apparatus further includes a third frequency image generating circuitry, for example. The third frequency image generating circuitry subtracts the first frequency image data from image data and generates third frequency image data including a frequency component higher than the first frequency component. The second frequency image generating circuitry 153 subtracts the third frequency image data from the image data and generates the second frequency image data including a frequency component higher than the first frequency component.

In the above-described first and second embodiments, information such as the standard deviation of noise based on a pixel value is preliminarily stored; however, embodiments are not limited thereto. For example, such a case may be conceived that determines threshold by acquiring a condition for collecting image data from the medical image diagnostic apparatus 200 via a network and generates a low-frequency image.

In each of the above-described first and second embodiments, an X-ray image is used as a medical image; however, embodiments are not limited thereto. Instead, a computer tomography (CT) image, a magnetic resonance (MR) image, an ultrasonic image, and others may be used as an object of processing, for example.

Furthermore, in the above-described embodiments, the image processing apparatus 100 detects a linear signal; however, embodiments are not limited thereto. Instead, the medical image diagnostic apparatus 200 may detect a linear signal, for example. The image processing apparatus 100 may be incorporated in the medical image diagnostic apparatus 200, for example. In other words, the medical image diagnostic apparatus 200 may include the data acquiring circuitry 151, the first frequency image generating circuitry 152, the second frequency image generating circuitry 153, the signal detecting circuitry 154, and the display image generating circuitry 155 and perform the above-described processing.

For example, in such a case where an X-ray diagnostic apparatus (such as an X-ray angiography apparatus) serving as the medical image diagnostic apparatus 200 includes therein the image processing apparatus 100 and detects a linear signal, an image with higher visibility can be generated from the linear signal derived from a guidewire, a catheter, and others used for interventional treatment. The treatment time and the amount of exposure can be accordingly reduced in this manner.

Figure 12:
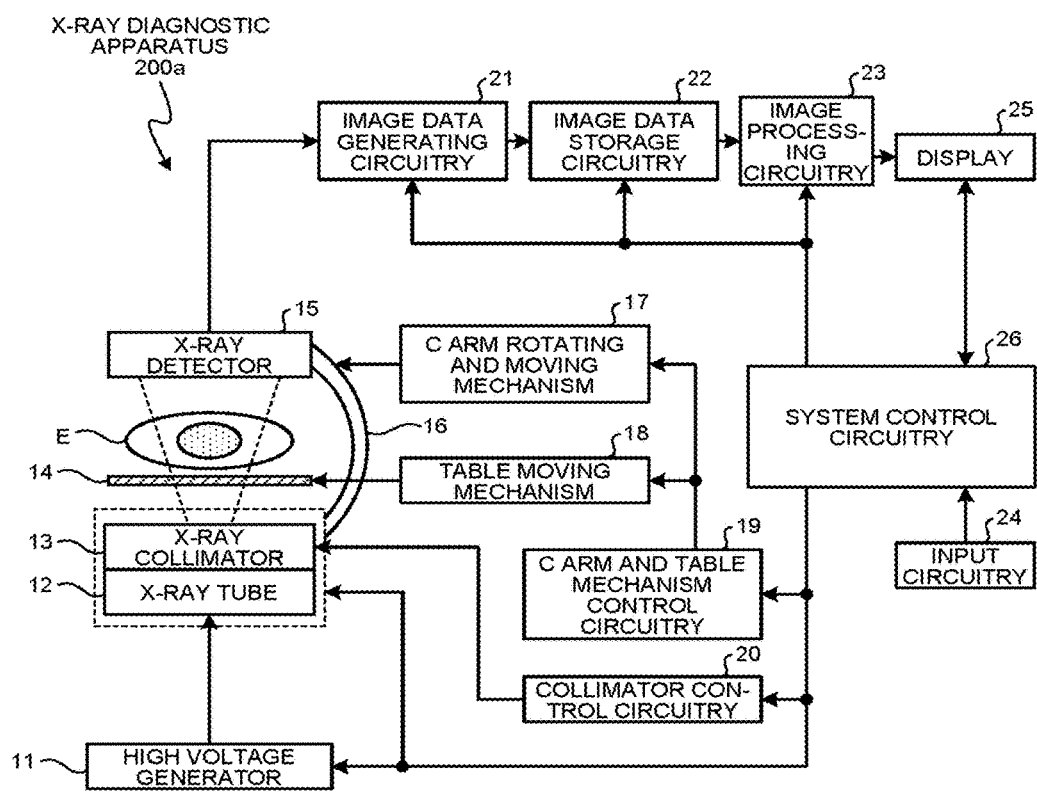
FIG. 12 is a drawing that illustrates an exemplary configuration of an X-ray diagnostic apparatus according to a third embodiment.

An X-ray diagnostic apparatus performing the above-described processing will now be described with reference to FIG. 12. FIG. 12 is a drawing that illustrates an exemplary configuration of an X-ray diagnostic apparatus 200a according to a third embodiment. As illustrated in FIG. 12, the X-ray diagnostic apparatus 200a according to the third embodiment includes a high voltage generator 11, an X-ray tube 12, an X-ray collimator 13, a table 14, an X-ray detector 15, a C arm 16, a C arm rotating and moving mechanism 17, a table moving mechanism 18, a C arm and table mechanism control circuitry 19, a collimator control circuitry 20, an image data generating circuitry 21, an image data storage circuitry 22, an image processing circuitry 23, an input circuitry 24, a display 25, and a system control circuitry 26.

The high voltage generator 11 generates g voltage and supplies the generated voltage to the X-ray tube 12. The X-ray tube 12 is an X-ray source generating X-rays using the high voltage supplied from the high voltage generator 11. The high voltage generator 11 adjusts voltage to be supplied to the X-ray tube 12, thereby adjusting the amount of X-ray irradiation to a subject E and controlling on and off states of the X-ray irradiation. The X-ray collimator 13 is a device for concentrating X-rays generated by the X-ray tube 12 so that an area of interest on the subject E will be selectively irradiated with the X-rays. For example, the X-ray collimator 13 has slidable collimator blades. The X-ray collimator 13 slides the collimator blades, concentrates X-rays generated by the X-ray tube 12, and irradiates the subject E with the X-rays.

The table 14 is a bed where the subject E is laid and is placed on a table mechanism (not illustrated). The X-ray detector 15 is a device where a plurality of X-ray detecting elements for detecting X-rays having penetrated the subject E are aligned in a matrix form. Each of the X-ray detecting elements of the X-ray detector 15 converts X-rays having penetrated the subject E into an electric signal, stores the signal, and transmits the stored electric signal to the later-described image data generating circuitry 21. The arm 16 is an arm in the shape of C for holding the X-ray tube 12, the X-ray collimator 13, and the X-ray detector 15. The C arm 16 holds these devices in a manner of having the X-ray tube 12 and the X-ray collimator 13 face the X-ray detector 15 so that the subject E will be laid therebetween.

The C arm rotating and moving mechanism 17 is a device for rotating and moving the C arm 16. The table moving mechanism 18 is a device for moving the table 14. The C arm and table mechanism control circuitry 19 is a processing circuitry that adjusts rotation and a move of the C arm 16 and adjusts a move of the table 14 by controlling the C arm rotating and moving mechanism 17 and the table moving mechanism 18. The collimator control circuitry 20 is a processing circuitry that adjusts the aperture level of the collimator blades of the X-ray collimator 13 and controls the irradiation range of X-rays.

The image data generating circuitry 21 is a processing circuitry that generates an X-ray image using an electric signal converted from X-rays having penetrated the subject E by the X-ray detector 15 and stores the generated X-ray image in the image data storage circuitry 22. Specifically, the image data generating circuitry 21 performs current and voltage conversion, analogue and digital conversion, and parallel and serial conversion on the electric signal transmitted from the X-ray detector 15 and generates an X-ray image. The image data storage circuitry is a storage device that stores the X-ray image generated by the image data generating circuitry 21. Examples of the image data storage circuitry 22 include a semiconductor memory element such as a random access memory (RAM) and a flash memory, a hard disk, and an optical disk.

The image processing circuitry 23 is a processing circuitry that performs various kinds of image processing on an X-ray image stored in the image data storage circuitry 22. For example, the image processing circuitry 23 performs smoothing filtering processing for reducing noise on the X-ray image. Examples of the image processing circuitry 23 include an integrated circuit such as an application specific integrated circuit (ASIC) and a field programmable gate array (FPGA) and an electronic circuit such as a central processing unit (CPU) and a micro processing unit (MPU).

The input circuitry 24 is an input device that receives various kinds of commands from an operator such as a doctor and a technician operating the X-ray diagnostic apparatus 200a and forwards the received command to the system control circuitry 26. For example, the input circuitry 24 has a mouse, a keyboard, a button, a trackball, a joystick, and the like for receiving various kinds of commands from an operator. The display 25 is a display that displays a graphical user interface (GUI) for receiving a co and from an operator through the input circuitry 24, an X-ray image stored in the image data storage circuitry 22, an X-ray image where the image processing circuitry 23 has performed image processing, and the like. Examples of the display 25 include a liquid crystal display and a cathode-ray tube (CRT) display.

The system control circuitry 26 is a processing circuitry that controls the overall operation on the X-ray diagnostic apparatus 200a. Examples of the system control circuitry 26 include an electronic circuit such as a central processing unit (CPU) and a micro processing unit (MPU). The system control circuitry 26 controls, for example, the high voltage generator 11, the C arm and table mechanism control circuitry 19, and the collimator control circuitry 20 according to a command of the operator forwarded from the input circuitry 24, thereby adjusting the amount of X-rays, controlling on and off states of X-ray irradiation, adjusting rotation and a move of the C arm 16, adjusting a move of the table 14, and the like.

The system control circuitry 26 controls image generating processing performed by the image data generating circuitry 21 and image processing performed by the image processing circuitry 23 according to a command from the operator. The system control circuitry 26 controls a GUI for receiving a command from the operator, an X-ray image stored in the image data storage circuitry 22, an X-ray image where the image processing circuitry 23 has performed image processing, and others to be displayed on a monitor of the display 25.

For example, the image processing circuitry 23 includes the first frequency image generating circuitry 152, the second frequency image generating circuitry 153, the signal detecting circuitry 154, and the display image generating circuitry 155 in the above description and performs the above-described processing on an X-ray image read out from the image data storage circuitry 22. In other words, the first frequency image generating circuitry 152 generates first frequency image data including a specific contrast component and a first frequency component on the X-ray image by performing, on an object pixel of processing, processing based on pixel values of neighboring pixels positioned close to the object pixel. The second frequency image generating circuitry 153 performs processing of subtracting the first frequency image data from the X-ray image and generates second frequency image data including a second frequency component. The signal detecting circuitry 154 detects a linear signal derived from a linear structural object from the second frequency image data. The display image generating circuitry 155 generates a display image according to the linear signal detected by the signal detecting circuitry 154. In this manner, the X-ray diagnostic apparatus 200a generates an image with higher visibility from the linear signal and has the display 25 display the image. The X-ray diagnostic apparatus 200a may further include the data acquiring circuitry 151 and perform the above-described processing on an X-ray image acquired from the image storage apparatus 300.

According to one or more of the embodiments described above, visibility of an image including a linear signal can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
processing circuitry configured to
generate first frequency image data including a contrast component, in which a difference between pixel values of neighboring pixels exceeds a threshold, and a first frequency component from image data,
generate second frequency image data including a second frequency component by subtracting the first frequency image data from the image data,
detect a linear signal derived from a linear structural object from the second frequency image data, and
generate a display image according to the linear signal detected.

2. The image processing apparatus according to claim 1, wherein the processing circuitry is configured to
define a frequency component lower than the second frequency component as the first frequency component and generates the first frequency image data including the first frequency component and the contrast component, and
subtract the first frequency image data from the image data to generate the second frequency image data including a frequency component higher than the first frequency component.

3. The image processing apparatus according to claim 1, wherein the processing circuitry is configured to set, as a pixel value of each pixel on the image data, an average of pixel values of neighboring pixels, the pixel values of which fall within a range based on a standard deviation of noise, among neighboring pixels positioned close to the pixel to generate the first frequency image data.

4. The image processing apparatus according to claim 1, further comprising:
a display configured to display the display image, wherein the linear structural object is a guidewire or a catheter to be inserted into a subject,
the processing circuitry is configured to sequentially generate the display image that is an X-ray image generated based on an X-ray having penetrated the subject, and
the display is configured to sequentially display the sequentially generated display image to display a video in real time.

5. The image processing apparatus according to claim 4, wherein the display displays the display image including the guidewire or the catheter inserted near a bone of the subject.

6. The image processing apparatus according to claim 1, wherein the processing circuitry is further configured to
generate third frequency image data including a frequency component higher than the first frequency component from the image data, and
generate the second frequency image data including a frequency component higher than the first frequency component by subtracting the third frequency image data from the image data.

7. A medical image diagnostic apparatus, comprising the image processing apparatus according to claim 1.

8. An X-ray diagnostic apparatus, comprising:
processing circuitry is configured to
collect image data,
generate first frequency image data including a contrast component in which a difference between pixel values of neighboring pixels exceeds a threshold and a first frequency component from the image data,
generate second frequency image data including a second frequency component by subtracting the first frequency image data from the image data,
detect a linear signal derived from a linear structural object from the second frequency image data, and
generate a display image according to the linear signal detected.

* * * * *